United States Patent [19]

Spaulding

[11] Patent Number: 5,648,468
[45] Date of Patent: Jul. 15, 1997

[54] PROCESS FOR IDENTIFYING SEX ASSOCIATED EGG PROTEINS AND METHODS FOR INCREASING THE PROBABILITY THAT THE AVIAN OFFSPRING WILL BE THE DESIRED SEX

[76] Inventor: Glenn F. Spaulding, 4049 Via Marina, M115, Marina Del Ray, Calif. 90292

[21] Appl. No.: 310,439

[22] Filed: Sep. 22, 1994

Related U.S. Application Data

[63] Continuation-in-part of Ser. No. 58,230, May 10, 1993, abandoned, which is a continuation-in-part of Ser. No. 490,930, Mar. 9, 1990, abandoned.

[51] Int. Cl.$^6$ .................... C07K 1/00; A61K 35/52
[52] U.S. Cl. .................. 530/359; 530/350; 530/367; 530/368; 530/389.1; 530/412; 530/827; 530/852; 530/853; 424/561
[58] Field of Search .................... 530/359, 350, 530/367, 368, 389.1, 412, 827, 852, 853; 435/2; 424/561

[56] References Cited

U.S. PATENT DOCUMENTS

| | | | |
|---|---|---|---|
| 3,692,897 | 9/1972 | Bhattacharya et al. | 424/85.8 |
| 4,327,177 | 4/1982 | Shrimpton | 435/2 |
| 5,021,244 | 6/1991 | Spaulding | 424/561 |
| 5,055,397 | 10/1991 | Kwoh et al. | 435/6 |
| 5,080,895 | 1/1992 | Tohoro | 424/85.8 |
| 5,135,759 | 8/1992 | Johnson | 424/561 |

OTHER PUBLICATIONS

Mizuno et al, *Manipulation of the Avian Genome*, Ed. Etches et al, A.M.V. CRC. Chapter 17, pp. 257–274, 1993.
Belote et al, *Cell*, vol. 40, pp. 339–348, Feb. 1985.
Towbin et al, *Proc. Natl. Acad. Sci. USA*, vol. 76, No. 9, pp. 4350–4354, Sep. 1979.
Kido et al, *Biochem J.*, vol. 286, pp. 17–22, 1992.
Zhai, *Chemical Abstracts*, vol. 119, p. 564, Ref. #45487f, 1993 (Kundrong Xuebao, 1993, 36(1) 113–215).
Calder et al, *Veterinary Record*, vol. 133, pp. 247–248, 1993.
Deeley et al, *Manipulation of the Avion Genome*, Ed. Etches et al, A.M.V. CRC. Chapter 13, pp. 205–222, 1993.
Eyal-Giladi et al, *Manipulation of the Avian Genome*, Ed. Etches et al, A.M.V. CRC, Chapter 3, pp. 29–37, 1993.
Fichtali et al, *Journal of Food Science*, vol. 58, No. 6, pp. 1282–1285, 1993.
Gassmann et al, *The FASEB Journal*, vol. 4, pp. 2528–2532, May 1990.
Gibbins, *Manipulation of the Avian Genome*, Ed. Etches et al, AMV, CRC, Chapter 19, pp. 285–309, 1993.
Parkhurst et al, *Poultry Meat and Egg Production*, AVI, pp. 68–69, 1988.
Tsang et al, *Poultry Science*, vol. 62, pp. 1297–1304, 1983.
Zijpp et al, *Poultry Science*, vol. 65, 809–811, 1986.

*Primary Examiner*—Cecilia Tsang
*Assistant Examiner*—Abdel A. Mohamed

[57] ABSTRACT

A method for Avian sex-preselection by identifying sex-specific proteins for maternal immunization to embryonic proteins is described. Sex-preselection proteins are used in sexing offsprings.

1 Claim, 1 Drawing Sheet

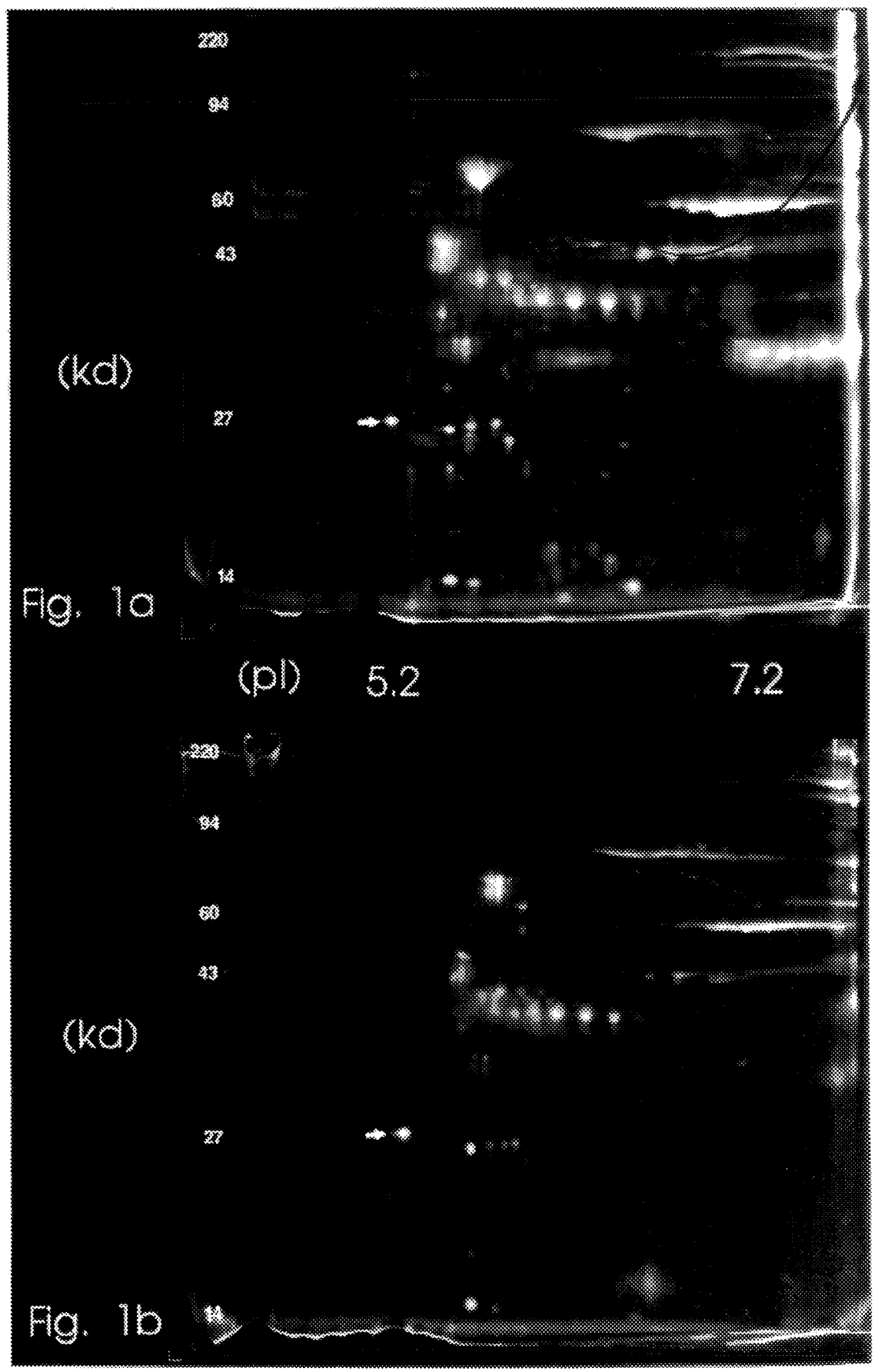

PROCESS FOR IDENTIFYING SEX ASSOCIATED EGG PROTEINS AND METHODS FOR INCREASING THE PROBABILITY THAT THE AVIAN OFFSPRING WILL BE THE DESIRED SEX

CROSS-REFERENCES TO RELATED APPLICATIONS

This application is a continuation-in-part of Applicant's application Ser. No. 08/058/230, filed May 10, 1993, which was a continuation-in-part of Ser. No. 07/490,930, filed Mar. 3, 1990 both now abandoned.

REFERENCES CITED

U.S. Pat. Nos.

| | | |
|---|---|---|
| 3,692,897 | Bhattacharya et al. | 9/19/72 |
| 5,021,244 | Spaulding | 5/12/89 |
| 5,080,895 | Tokoro | 1/14/92 |

Publications:

Belote J. M., Handler A. M., Wolfner M. F., Livak K.J., and Baker B. S. Sex-specific Regulation of Yolk Protein Gene Expression in Drosophila. Cell. 40. 339–348. Feb. 1985.

Bradford, M., ANAL. BIOCHEM., 72: 248, 1976

Calder, M. R. and R. Rajamahendra. Altered Sex ratio following immunisation of female mice with male splenic cells. Veterinary Record. 133. 247–248, 1993.

Deeley, R. G., R. A. Burtch-Wright, C. E. Grant, P. A. Hoodless, A. K. Ryan, and T. J. Schrader. Synthesis and deposition of egg proteins. Manipulation of the Avian Genome, Ed. Etches, R. J. and Gibbins, A. M. V. CRC. Ch. 13. 1993.

Eyal-Giladi, H. Early determination and morphogenetic processes in birds. Manipulation of the Avian Genome, Ed. Etches, R. J. and Gibbins, A. M. V. CRC. Ch. 3. 1993.

Fichtali, J., E. A. Charter, K. V. Lo, and S. Nakai. Purification of antibodies from industrially separated egg yolk. Journal of Food Science. 58(6). 1282–1285. 1993.

Gassmann, M., P. Thomroes, T. Weiser, and U. Hubscher. Efficient production of chicken egg yolk antibodies against a conserved mammalian protein. The FASEB Journal. 4. 2528–2532. May. 1990.

Gibbins, A. M. V. Future interactions between molecular biologists and the poultry industry, illustrated by a comparison of the genome mapping and gene targeting paradigms. Manipulation of the Avian Genome, Ed. Etches, R. J. and Gibbins, A. M. V. CRC. Ch. 19. 1993.

Hames, B. D. and D. Rickwood. Gel Electrophoresis of Proteins: A Practical Approach. Second Edition. Irl Press at Oxford University Press. 1990.

Mizuno, S., Y. Saitoh, O. Nomura, R. Kunita, K. Ohtomo, K. Nishimori, H. Ono, and H. Saitoh. Sex-specific DNA sequences in galliformes and their application to the study of sex differentiation. Manipulation of the Avian Genome, Ed. Etches, R. J. and Gibbins, A. M. V. CRC. Ch. 17. 1993.

Oakley, B. R., Dirsch, D. R. and Moris, N. R., ANAL. BIOCHEM., 105: 361–363, 1980

O'Farrel, P. H., J. BIOL. CHEM., 250: 4007–4021, 1975

Parkhurst, C. R. and G. J. Mountney. Poultry Meat and Egg Production. AVI. pg. 68–69. 1988.

Towbin et. al., Electrophoretic transfer of proteins from ployacrylamide gels to nitrocellulose sheets: procedure and some applications Proc. Nat. Acad. Sci. 76. 1979

Tsang, C. P. W. and A. A. Grunder. Effect of active immunization against estradiol on egg shell quality. Poultry Science. 62. 1297–1304. 1983

Zijpp, A. J. van der, T. R. Scott, and B. Glick. The effect of different routes of antigen administration on the humoral immune response of the chick. Poultry Science. 65. 809–811. 1986.

BACKGROUND OF INVENTION

It has long been realized that there are distinct marketing and manufacturing advantages if one had the ability to control sex of the offspring in birds. Hens have the advantage over roosters for laying eggs. Roosters have the advantage over hens for meat production. Currently there is a 50% chance of obtaining the desired sex. For birds the sex of the offspring is determined by the female, male sperm have a homogenous sex chromosome content. This is in sharp contrast to mammals where sperm has a heterogenous sex chromosome content, bearing either the X-chromosome or the Y-chromosome. Consequently, avian females have haploid chromosomal diversity in the eggs. It has been demonstrated in Drosophila that there is a sex-specific initiation and maintenance of yolk protein synthesis, which may be conserved in chickens (Belote et al., 1985). Much of the egg yolk is synthesized by the adult female liver then added to the egg. Little is know about the post-translational changes that take place in yolk proteins as regulated by the haploid egg. Nothing is known about sex-specific protein contributions by the haploid cells that are a part of the egg or the early embryonic cell contributions. No one until now has identified those protein constituents. Bhattacharya et al. (U.S. Pat. No. 3,692,897) refers to an immunological method for controlling the sex of mammalian offspring, making use of spermatozoa which has been previously separated into fractions having the desired sex characteristics. He defines the sex as sperm that are genotypically known to contain X chromosomes which carry female producing genes, while others contain Y chromosomes which carry male producing genes. The claims and invention addresses antibodies reactive to X-sperm or Y-sperm from mammalian ejaculates. He does not anticipate or make obvious claims associated with avian germ cells nor does his invention refer to modifying eggs. Said antigens were derived from sperm and subsequent immunizations were to sperm immunogens. A method for isolating egg protein fractions or egg protein fractions from karyotyped avian eggs was not taught. The techniques herein described are available commercially, described in Gel Electrophoresis of Proteins: A Practical Approach and/or described in U.S. Pat. No. 5,021,243 to Spaulding.

Weak sex selection pressures will translate into large yields because poultry production is so large. There are several billion chickens produced every year. If sex selection pressures were weak, for example only affecting 1 birth in a 1000, those weak pressures would still improve the sex selection outcome by several million chickens per year. Therefore, weak selection pressures are amplified because the production numbers are so large. A novel approach for increasing the probability that a hen will have a specific sex offspring is described herein. The approach identifies embryonic sex-specific proteins. Those proteins are used in a vaccine for the hen. A vaccinated hen will transfer antibodies to the egg. Antibodies to sex-specific proteins in the egg will impede embryonic development thereby changing the sex selection pressures. Or, antibodies to sex-specific protein or sex-specific proteins could be used diagnostically. An approach for improving sex selection pressures similar to this approach has been successful in mammals (Calder and Rajamahendra, 1993). Their approach used mammalian spleen H-Y autoantigens in the vaccine.

Sex preselection pressures can be imposed through different approaches. One approach would be to vaccinate a hen with a sex-specific protein or a plurality of proteins. Antibodies, to sex-specific proteins, would transfer to the egg. As the embryo develops, it produces a new set of proteins that are distinct from the maternal set. Those sex-specific proteins are disclosed herein. Antibodies to evolving sex-specific proteins would impede embryogenesis by antibody sequestration thereby adding a selection pressure. Alternatively, testing the egg yolk for the presents of sex-specific proteins would provide information to decide which egg should be placed into an incubator. If females were the preferred sex, the yolk could be assayed for female sex-specific protein patterns using gel electrophoresis. Or, antibodies raised to sex-specific proteins could be used in an immunodetection assay. Either test would inform the producer about the sex of the egg.

A female ovum determines the sex of the offspring (Mizuno et. al., 1993), which is the opposite for mammals (U.S. Pat. No. 3,692,897; U.S. Pat. No. 5,021,244). Yolk proteins are synthesized by the maternal liver. Others yolk constituents are transferred from the maternal plasma. Therefore, it does not matter whether the egg is female or male they both start out with the same maternal complement of protein (Deeley et. al., 1993). A electrophoretic protein profile of a male or female egg, before embryonic development, would appear similar (a similar developmental identification system has been applied to identifying sex-specific proteins in mammalian sperm U.S. Pat. No. 5,080,895). The electrophoretic profiles would appear similar because the egg yolk proteins came from the same mother. Eggs begin with similar protein constituents. Later, as the embryo develops, unique stage specific proteins are expressed. Unique proteins would appear as unique spots or lines on a protein electrophoretogram. The proteins which are not unique, would appear as common spots seen on both female and male electrophoretograms (U.S. Pat. No. 5,080, 895). Those unique proteins are associated with enabling development of organ systems. Sex-specific characteristics are seen early in the embryo (Deeley et. al., 1993; Mizuno et. al., 1993). Chromosomes for sex differentiation, expressed in stages during embryonic development, can be male or female specific, and may not be expressed in the adult (Deeley et. al., 1993; Mizuno et. al., 1993). The protein products of sex determination in poultry have not been reported, only the DNA specific expression has been reported (Mizuno et. al., 1993). It is known by those skilled in the art that there many proteins expressed during embryogenesis. Many of those proteins that are expressed during embryogenesis are unique to the embryo and not expressed in the adult. Each protein is vital. Progression from one stage to the next requires the orchestration of a complex set of proteins and cellular events (Eyal-Giladi, 1993). A loss or diminution of one protein type can have fatal consequences. Diminution may take the form of a single amino acid substitution that reduces the potency or the decreased production of a particular protein. The literature is replete with, and those skilled in the art are cognizant of, many diseases where reduced availability of a single protein has catastrophic consequences. It is also known that embryos are the most fragile and susceptible to aberrancies. Antibodies to sex-specific proteins would impose a selection pressure during a fragile period (Calder and Rajamahendra, 1993); a slight selection pressure would be amplified by the amount of poultry produced per year. Immunization methods for poultry are well known by those skilled in the art (Tsang and Grunder, 1983; Zijpp et. al., 1985; Gassmann et. al., 1990; U.S. Pat. No. 5,021,244). Maternal antibodies accumulate in the egg yolk in higher concentrations than maternal serum, and because of that characteristic, investigators have proposed eggs as a source for industrial production of antibodies (Fichtali et. al., 1993). There are two other unique features of poultry vaccination. Chickens have the potential to mount an antibody response to conserved mammalian protein (Gassmann et. al., 1990). Moreover, a hen can be vaccinated with an autoantigen (estradiol) and the antibodies will interfere with egg shell production (Tsang and Grunder, 1983). The route of antigen administration does not appear to affect the immune response (Zijpp et. al., 1985). Thus, hens have been vaccinated to autoantigens; the immune response has been shown to inhibit a growth function and change selection pressures. Antibodies from the female are passed to the yolk in large quantities. Yolk transmitted antibodies are highly resistant to degradation (Fichtali et. al., 1993). During embryonic development germinal cells are move into the yolk sac (Eyal-Giladi, 1993). Egg yolk antibodies are transferred to the embryo. The yolk is protected from kidney excretions by the allantois (Parkhurst and Mountney, 1988). Therefore, electrophoretograms of egg yolk proteins would have spots common to both males and females; for common metabolic and developmental pathways. Unique spots would represent sex-specific proteins when egg yolk sampling was similar except for sex segregation. Some of the sex-specific genes are known to be transcribed during embryogenesis but the protein translations are unknown.

It is well known by those skilled in the art and the subject of hundreds of articles, how to separate a protein from a mixture of proteins, isolate the separated protein, use the isolated protein in a vaccine and use the antibodies for diagnostic immunoassays (Belote et. al, 1985; Bradford et. al., 1976; O'Farrel et. al., 1975; Oakley et. al., 1980; Towbin, 1979; Tsang and Grunder, 1983; Zijpp et. al., 1985; Gassmann et. al., 1990; U.S. Pat. No. 5,080,895; U.S. Pat. No. 5,021,244).

FIELD OF INVENTION

The field of this invention is the isolation of novel proteins, the generation of avian antibodies to said proteins and their use in methods to increase the probability that avian offspring produced by the process will be of a desired sex or carry a gene for a particular sex-chromosome linked trait. More particularly, this invention relates to sex-associated egg proteins and other haploid expressed proteins in birds and to antibodies which bind to them. It relates to the immunization of birds with said novel sex-specific proteins so to increase the probability that an offspring will have the desired sex-chromosome linked trait. The protein sequence information and DNNRNA information thereby derived can be utilized to develop avian strains that reproduce offspring of a single sex or sex-linked trait.

Sex-specific proteins can be isolated by a variety of methods. The identification of specific protein patterns can be used to determine the sex of an egg. Proteins isolated from separation pattern can be used to raise antibodies to those proteins in a variety of species. Antibodies to sex-specific proteins can be used in immunoassays for sex determination. Autologous antibodies can be injected back into the hen to boost the concentration of antibodies transferred to the egg and, therefore, the sex selection pressure.

SUMMARY OF THE INVENTION

Egg protein is obtained from karyotyped chicken embryos. The proteins are separated by 2-dimensional gel electrophoresis. Those proteins that are unique to the male embryo are designated sex-specific male, those unique to the female are designated sex-specific female. Said identified proteins can be isolated. Substantially pure (defined as at least as pure as obtained by the 1-dimension gel isolation techniques) male or female unique proteins can be used in avian female immunization protocols so to generate maternal antibodies. Maternal antibodies to haploid unique sex-specific egg proteins can prevent the development of a specific sex of offspring or sex linked trait.

Antibodies raised to sex-specific proteins can be used in a wide variety of commercial kits (e.g.; Sigma, St. Louis, Mo.) to detect for the presents of sex-specific proteins. With knowledge of the sex of an egg commercial producer can decide the fate of that egg. Knowledge of sex-specific protein patterns of expression can lead to transgenic chickens that produce single sexed eggs.

BRIEF DESCRIPTION OF THE DRAWING

FIG. 1a is a 2-dimensional electrophoretic separation of protein from a karyotypic female chicken egg that is silver stained. FIG. 1b is a 2-dimensional electrophoretic separation of protein from a karyotypic male chicken egg that is silver stained. The general location of the molecular weight markers (MW) are denoted as are points of a representative pH profile as measured by surface pH electrode.

DETAILED DESCRIPTION OF INVENTION

In one embodiment, five and six day old chicken embryos are karyotyped by contract service (Medical Center, San Antonio, Tex.) using standard methods. Briefly, the eggs are dissected and 1–2 ml of egg yolk removed and frozen (–20 degrees C.). Remaining cells are cultured in media so to obtain metaphase cells for karyotyping. Egg yolk (or egg proteins) from a karyotypic male and female can be electrophoretically separated for protein analysis. In one embodiment, the egg yolk samples are analyzed (by commercial contract—Kendrick Lab., Madison, Wisc.) for total protein content using the Coomassie Blue Binding method of Bradford (1976)(Gel Electrophoresis of Proteins: A Practical Approach, 1990)(Kendrick Laboratories, Madison, Wisc.). Equal amounts of the sample were completely dissolved by placing the sample in sample buffer and boiling in a water bath for 10 minutes. Two-dimensional electrophoresis is performed according to the method of O'Farrel (1975)(Gel Electrophoresis of Proteins: A Practical Approach, 1990) by Kendrick Labs, Inc. (Madison, Wisc.) as follows: Isoelectric focusing is carried out in glass tubes of inner diameter 2.0 mm, using 2% certified Resolytes pH 4–8 ampholines (BDH from Hoefer Scientific Instruments, San Francisco, Calif.) for 9600 volt-hrs. Forty ng of an isoelectric focusing (IEF) internal standard, vitamin D dependent calcium binding protein, MW 27,000 and isoelectric focusing point (pI) 5.2 is added to the samples. This standard is indicated by an arrow on the stained 2-dimensional gel (FIGS. 1a & 1b). The final tube gel pH gradient extends from about pH 4 to pH 8 as measured by a surface pH electrode (FIG. 2).

After equilibration for 10 minutes in SDS sample buffer (10% glycerol, 50 mM dithiothreitol, 2.3% SDS and 0.0625 M tris, pH 6.8) the tube gels are sealed to the top of 10% acrylamide slab gels (0.75 mm thick) and SDS slab gel electrophoresis (SDS/PAGE) carried out for about 4 hours at 12.5 mA/gel. Voltage to the slab gel is turned off when the bromophenol dye front had reaches the bottom of the slab gel. The slab gels are fixed in a solution of 10% acetic acid/50% methanol overnight. The following proteins (e.g.; Sigma Chemical Co., St. Louis, Mo.) are added as molecular weight standards to the agarose which sealed the tube gel to the slab gel: myosin (220,00), catalase (60,000), vitamin D calcium binding protein (27,000) and lysozyme (14,000). These standards appear as fine horizontal lines on the silver stained 10% acrylamide slab gel. In one embodiment, the silver stain kit can be purchase from Sigma Chemical (St. Louis, Mo.). The silver stained gel is dried between sheets of cellophane with the acid edge to the left.

To identify sex-specific proteins a silver stained 2-dimensional gel derived from a karyotypic male egg is compared with a similar gel from a karyotypic female egg. Although the protein loads are assayed prior to loading onto the gel, the gel-to-gel silver stained integrated intensity retains some variability. So to accommodate the variability, the mean spot integrated intensity can be normalized with instrumentation (e.g.;BioImage, MI, or available from Kendrick Laboratories, Madison, Wisc.) or alternately can be visually normalized by one with ordinary skill in the art. It becomes obvious to one skilled in the art which proteins are abundant or lacking when compared to the companion gel of opposite sex. Said proteins that are uniquely abundant in one gel but lacking in the companion gel are designated sex-specific proteins. Those proteins are the object of interest for developing sex-specific antibodies in the immunized bird— immunized with said protein. In an alternate embodiment, a combination of sex-specific proteins can be utilized to improve the immunogenic response. Examination of the 2-dimensional gels reveals many spots which appeared on one profile but not on the other. In some cases, the absence of a spot indicates a protein whose intensity is below the range of sensitivity for detection. Clearly, one of ordinary skill in the art could visualize these proteins by loading more sample on the gel or by using more sensitive staining techniques. One skilled in the art can take the MW information and surface pH information and interpolate pI and MW for specific sex-specific proteins by using a ruler or specifically designed instrument (e.g.; BioImage, Mich.). It is clear that the knowledge that said sex-specific proteins exist enables others skilled in the art to employ different protein isolation and separation techniques to isolate said proteins or identify their sequences (e.g.; capillary electrophoresis, subtractive hybridization, etc.). This is not intended to exhaust the entire class of sex-specific proteins more, undoubtedly, exist. Then, using the techniques advanced in this invention, one could identify which among these are sex-specific proteins (Table 1).

TABLE 1

| Male Sex-specific Proteins | | Female Sex-specific Proteins | |
| --- | --- | --- | --- |
| Molecular Weight | pI | Molecular Weight | pI |
| 85,000 | 8.0 | 130,000 | 5.0–5.9 |
| 63,000 | 6.4 | 47,000 | 6.3–7.1 |
| 57,000 | 6.4 | 30,000 | 6.3–6.8 |
| 35,000 | 7.3 | 29,000 | 7.0 |
| 29,000 | 5.3 | 15,000 | 5.5 |
| 10,000 | 6.3 | 15,000 | 5.4 |
| 10,000 | 6.1 | 10,000 | 5.8 |
| | | 10,000 | 5.1 |
| | | 6,000 | 5.3 |

Electrophoretically separated proteins can be transferred from the electrophoresis gel on to nitrocellulose (NC) using standard methods (Towbin et al., 1979) (Gel Electrophoresis of Proteins: A Practical Approach, 1990). In this technique, one positions the gel and NC sheets adjacent to one another, and applies a constant electric current to transfer all of the protein bands on the gel to the NC sheets, maintaining their relative positions. In one embodiment, the transfer can be performed using SDS/PAGE 1 dimensional or 2 dimensional gels in the presence of 25 mM Tris, 192 mM glycine, and 20% methanol using 250 mA of constant current for about 16 hours at 40° C. Following the transfer, the NC can be stained to detect the proteins with 0.5% amido black in 7% acetic acid. Amido black (Sigma Chemical, St. Louis, Mo.) is preferred because it does not interfere with the subsequent preparation of anti-sera or hybridomas from proteins. This process is available commercially (Kendrick Labs, Inc, Wisc.) or the chemicals are available (Sigma Chemical, St. Louis, Mo.). The separated, substantially purified sex-specific protein isolated on nitrocellulose can be surgically implanted into chickens.

In the embodiment of this invention using SDS/PAGE gels, to identify the sex-specific proteins that are transblotted to NC, a silver stained profile of the SDS/PAGE gel with incorporated MW and/or pl markers (Sigma Chemical, St. Louis, Mo.) can be aligned with amido black stained NC sheets. The alignment helps in the matching and correspondence of proteins. The amido black stained sex-specific proteins can then be isolated with a razor blade for sequencing or immunization. Sequencing can be contracted commercially (e.g.: Kendrick Labs, Inc.) and is generally known in the art. In an alternate embodiment, PVDF is substituted for NC for sequencing.

The cutout proteins can be used to raise antibodies to said proteins (Gel Electrophoresis of Proteins: A Practical Approach, 1990). The cutouts of NC can be surgically implanted to raise antibodies. Alternatively, the proteins in said bands are extracted with a suitable solvent, such as dimethylsulfoxide (DMSO) and can be injected into chickens. In such an extraction, the NC band is mixed with 100 microliters of DMSO. Then the solvent/NC mixture is mixed with 1 ml of adjuvant (e.g.: Freund's complete) prior to injection to raise antibodies. It is preferred that 100 micrograms of protein serve as the immunogen. Injections can be given subcutaneous every 4 days for 16 days (5 times) or every 2 weeks for 2 months. In an alternate embodiment, immunogenic epitopes can be synthesized based on sequence information from said isolated sex-specific proteins and substituted for the native isolate. It is known in the art that by immunizing the maternal avian parent, antibodies will appear in the egg that specifically bind to the original immunogen. To test the quality of the immunization protocol, blood can be withdrawn from the immunized animal and tested for protein specific activity. A 1 ml sample of blood can be withdrawn from the immunized bird utilizing immunization protocols herein described. The sample is allowed to clot and centrifuged to remove cellular material and clot. The antisera is collected and an NC transblot containing sex-specific protein (which is pre-blocked in low fat milk for 1 hour) immersed into the antisera for 1 hour. The blot is rinsed with low fat milk 3 times and incubated with an enzyme conjugated anti-avian immunoglobulin (available commercially, e.g.; horseradish peroxidase conjugated (HRP)) for 1 hour. The blot is rinsed again this time with PBS followed by distilled water and; incubated in an HRP chromogenic substrate to detect binding activity (tetrazolium salt e.g.: TMB). The location of the chromogen highlighted antibody binding can be compared to the silver stained or amido black stained gels to evaluate specificity. Those sex-specific immunogens that induce antibodies that bind selectively to the sex-specific egg proteins, and are essentially free of cross reactivity with egg proteins from the opposite sex and non-sex-specific proteins are the subject of the invention. Essentially free is generally defined as having no visual cross-reactivity at 1:100 dilutions. Alternatively, there are many commercial facilities that will sequence the proteins and develop bacterial expression systems that will produce large amounts for immunization. By knowing the sequence, DNA modifications can be made and a transgenic avian strain established that reproduces a specific sex chromosome associated avian offspring.

Electrophoretic maps and vaccines of separated sex-specific egg yolk can be obtained as previously described, and can be obtained using similar methods as described in U.S. Pat. No. 5,021,244 and U.S. Pat. No. 5,080,895 incorporated herein by reference. Two-dimensional electrophoresis was chosen because of its unmatched resolving power and sensitivity. It has over 1000 times the resolution of High Pressure Liquid Chromatography (HPLC) and can distinctly separate proteins. Protein overlaps can be easily observed. Female sex-specific proteins are identified by comparing electrophoretograms from both sexes (FIG. 1a Female; FIG. 1b-Male) and finding spots that are not present on the opposing electrophoretogram. The same approach can be used for identifying male sex-specific proteins. In the preferred embodiment comparisons are made electronically using a BioImage Gel Scanner, Ann Arbor, Mich. The differences that were detected are listed in Table 1. To sex an egg, a 1 ul sample of egg yolk is drawn. The sample is processed as previously described. Electrophoretograms thereby obtained are analyzed visually or electronically for specific protein spots. Those electrophoretogram with spots having approximately the same molecular weight and pl as those found in Table 1 are assigned to that gender. One or more of the sex-specific proteins must be present to assign gender. Alternatively, antibodies raised to sex-specific proteins, using the methods previously described herein and elsewhere, can be incorporated into a commercial immunoassay kit (Sigma, St. Louis, Mo.) to assign gender to an egg. If the antibody panel consisting of antibodies raised to each protein or a plurality of proteins associated with a specific sex (Table 1) shows a positive reaction then the gender from which that panel of antibodies or specific antibody was derived, is assigned to the egg from which the sample was obtained. A positive reaction can be in the form of precipitation, calorimetric change, luminescence or other assays known by those skilled in the art.

Differently isolation techniques could be used to isolate sex-specific proteins. Knowing in advance the molecular weights and pls of sex-specific proteins would direct other isolation approaches. By bracketing the molecular weight of a specific protein and collect protein near that molecular weight the sex-specific protein could be isolated. In one embodiment, a molecular weigh isolation procedure would be used and all the proteins within a range of molecular weights collected. Those proteins collected by an alternate molecular weight isolation procedure would be processed for two-dimensional electrophoresis as described herein. Further collection procedures could be adjusted based on the molecular weight range seen on the two-dimensional separation and the presence of the sex-specific protein. Once the molecular weight offset between the two isolation procedures was determined, further isolation procedures would factor in the molecular weight offset. The same approach would apply to pl. Having the two-dimensional sex-specific standard facilitates the isolation and identification of sex-specific proteins by other isolation procedures.

The examples included are not intended to limit the scope of the present invention. Other substitutions, modifications and variations of the process of isolating sex-specific proteins, vaccinations of said proteins, and/or diagnostic assays are apparent to those skilled in the art without departing from the disclosure and scope of the invention.

I claim:

1. A sex-specific poultry egg yolk protein isolated and identified by two-dimensional electrophoresis, having a molecular weight and isoelectric point determined under denaturing and reducing conditions, and selected from the group consisting of 85 kD and 8.0 pI, 63 kD and 6.4 pI, 57 kD and 6.4 pI, 35 kD and 7.3 pI, 130 kD and 5.0 to 5.9 pI, 30 kD and 6.3 to 6.8 pI, and 29 kD and 7.0 pI.

* * * * *